(12) United States Patent
Hoehe et al.

(10) Patent No.: US 6,538,120 B1
(45) Date of Patent: Mar. 25, 2003

(54) GENOMIC SEQUENCE OF THE HUMAN μ-OPIOID RECEPTOR GENE AND THE VARIANTS, POLYMORPHISMS AND MUTATIONS THEREOF

(75) Inventors: Margret Hoehe, Berlin (DE); Birgit Wendel, Berlin (DE)

(73) Assignee: Max-Delbruck-Centrum für Molekulare Medizin, Berlin (DE)

( * ) Notice: Subject to any disclaimer, the term of this patent is extended or adjusted under 35 U.S.C. 154(b) by 0 days.

(21) Appl. No.: 09/355,709

(22) PCT Filed: Feb. 2, 1998

(86) PCT No.: PCT/DE98/00382
§ 371 (c)(1),
(2), (4) Date: Sep. 27, 1999

(87) PCT Pub. No.: WO98/33937
PCT Pub. Date: Aug. 6, 1998

(30) Foreign Application Priority Data

Feb. 3, 1997 (DE) .......................................... 197 03 925

(51) Int. Cl.[7] .......................... C07H 21/02; C07H 19/00
(52) U.S. Cl. ..................................... 536/23.1; 536/22.1
(58) Field of Search ............................. 435/6; 536/23.5, 536/23.1

Primary Examiner—Jeffrey Fredman
Assistant Examiner—Suryaprabha Chunduru
(74) Attorney, Agent, or Firm—Norris McLaughlin & Marcus

(57) ABSTRACT

The invention concerns the genomic sequence of the human μ opioid receptor gene and its variants, polymorphisms and mutations.

4 Claims, No Drawings

SEQUENCE LISTING

```
<160> NUMBER OF SEQ ID NOS: 7

<210> SEQ ID NO 1
<211> LENGTH: 2412
<212> TYPE: DNA
<213> ORGANISM: Artificial Sequence
<220> FEATURE:
<223> OTHER INFORMATION: Description of Artificial Sequence: Human
      Genomic Clone
<221> NAME/KEY: promoter
<222> LOCATION: (1)..(2412)
<223> OTHER INFORMATION: promoter of human  opiate receptor
```

<400> SEQUENCE: 1

```
tgtgttagtg agcagacctc ccttaggaac cttattacgg agtacaaagc taggagagta      60
aataaagtat attaaaaaat gcatacaaaa gatgacagaa tcaccattcc aaaagatctt     120
ggtggataag aatcatgaat tggatctaac aagatgtaac ttaaaagtga aaaaatctat     180
agtgttgtac tgagctccct ccaaagcaac tataaattta taggagatga aacatatgat     240
tcaccaggca taagaagaaa gtttccgtaa tcaaacacta ttgtatccat cttttttaaac    300
tccagctcct atcacagcac ctggtccaaa gcagatcttt agtatttgtg gaactggctt     360
ggattgtgtt taggaaattt tgtcattggt aaacctaagg agagtcaaga gaacaacgtg     420
accaaaaaat aaaactaaaa aaaaaaaaaa gggactttca ttgtactggt agaaagacaa     480
agtttataat ctggcttagt ttcttttttt gttgttgttt gttttttggt cagggcaaat     540
ttaggtcatt atttttaaca ctggaactgt agtttcagag cagatagaca aactatcaat    600
gagaatagat gaacagcaag gccactgaaa ggactcagaa ctacatctta taagaaacaa    660
ctgaatgatg ctaatgttta acttgcaaaa gagaaaactc agttgatttc aaatatatga    720
aatatagtgg taaggagtta tcacttatta agcaattact attgcaatgt atactcattt    780
aatcctgcta acagacatat gaggtgaata ttattagcct accctcgcct ttttttaagta    840
atgagaagac tgtcatcctg tagggtaaag taacatgtcc aaactcatac agctacaaag    900
ttacaaagct gatttataaa atgattgact ccaaggtcag gaattattat actgtgtctt    960
gtcttccaca tgaactaagc acaaaggaac tgaatgcagg cagacagatt tcagctcaat   1020
ataagagaat tgttacatta gttcatggaa gaatatgttt taaggtattt ttgttagtct   1080
ctaggaaatc tctgtaacat tttattgtgt aaattatatg ctttaatgta agaggataaa   1140
aataatagtg aacattggca aaatagccta tgattaatag agtttaccta tgagttatct   1200
gtttctaaga taaatgccaa aaaataatat tggaattaaa tgttcctttc aagatcttcc   1260
ctccctgctc cctgaaattg cagtgaattt ttcaagacca actgaggaca tgtattttca   1320
atgtttatgg ttaaaagata tgtacatgca cagatatata catgtacaga aatgagaatt   1380
acttcagaat tggtgttaac tttagaaaaa aaagaccaa gaacttactc ttggtattta   1440
caaatttatt tctaaaatag aagcactcat ggacttagaa gtaaggtata aaattcaaaa   1500
acgtatccat gtttctcaag gatcttgttg taggccactc taattccata tattatgtgg   1560
cttttcctag aattttttaca ctagaaaaca gactgaatgc aaattttgtt ttgttttaac   1620
aaccttcttc tcagaagcat atgtctatcg aggaagtctt cagataaaaa agataaacaa   1680
ttccaaacag gtctatgaga tttaagatgt gaaagatcaa cattatcttt agttgacttt   1740
actggatgcc acaaccttct gatttctgta accacttctt atgcctccta cccactgaaa   1800
caaaatcaga ggcaaacaga gcttcaccct agaaattggg gaaaatgagg aacaggtttt   1860
ctgcacaaaa gtttatttgt ttctcatttc ttttttcagaa aataaaggat cgctgttgtt   1920
cccaacaggt ttgtagggaa gaaaattgga gaaacattat tacctttttct tagatgttgg   1980
caacggaggc aacaaggact gcaaagaaaa attgtgtgtc ccccattcct aaataatcaa   2040
aattggcagt agggatggaa gagcattggg gttttagggc tgttagggtt tcatcaagcc   2100
aatgtattcc ctgccagatt ttaaggagaa aaaggcgctg gaaaattgag tgatgttagc   2160
cccctttctt attttttgcac tgctaccaaa gactaactct atctctctcc ccaacccttc   2220
tctccatctc cctcctttag atgtgtttgc acagaagagt gcccagtgaa gagacctact   2280
ccttggatcg ctttgcgcaa aatccacccc ttttccctcc tccctcccctt ccagcctccg   2340
```

```
aatcccgcat ggcccacgct cccctcctgc agcggtgcgg ggcaggtgat gagcctctgt    2400
gaactactaa gg                                                          2412

<210> SEQ ID NO 2
<211> LENGTH: 773
<212> TYPE: DNA
<213> ORGANISM: Artificial Sequence
<220> FEATURE:
<223> OTHER INFORMATION: Description of Artificial Sequence: Human
      Genomic Clone
<221> NAME/KEY: intron
<222> LOCATION: (1)..(773)
<223> OTHER INFORMATION: intron 2 of human  opiate receptor

<400> SEQUENCE: 2
gtgagtgatg ttaccagcct gagggaagga gggttcacag cctgatatgt tggtgatgtc      60
ataagcaaag cagtatttat ggagtgcccc attgtcttag tcacattgta attttaatta    120
ttcttcctag caaaaaaagc ctttgaatac ttaaaaatag gaattttcct cataatttta    180
ggcctattaa atcctttaaa gagaatgtaa tctatttatt tctgatttct ctgtatttac    240
ttcataaaaa tggtgtgtaa attagtacat agctctccca agagtaattg gagcttaaac    300
ccaaagagta ttacactgag gcttgtttaa aattatcaag tggctgacta catggcaaat    360
gtatctttct acacctaata tcagaatatt gaacaatcca tcaaaaaatg aagtgaaaac    420
atccattacc tggagccgcc tagagacttt ggacaattat tacatttttt atatcaatat    480
agacctcatg gaggatctag ctcatgttga gaggttcatt tttgttccct gaacgaaagc    540
ttaatgtgat cgaagtggac tgcaaaatgg gaaatttaga aaaaaacaaa aacattaga     600 agtaaaactt tctttgaaaa gtaacaaaca actgagtttc ttccacaatt tctttatagc    660
cttaagttag ctctggtcaa ggctaaaaat gaatgagcaa aatggcagta ttaacacctt    720
atgacataat taaatgttgc tgctaatttt tcctttaaat tcctttcttc tag            773

<210> SEQ ID NO 3
<211> LENGTH: 383
<212> TYPE: DNA
<213> ORGANISM: Artificial Sequence
<220> FEATURE:
<223> OTHER INFORMATION: Description of Artificial Sequence: Human
      Genomic Clone
<221> NAME/KEY: intron
<222> LOCATION: (1)..(383)
<223> OTHER INFORMATION: intron 1 of human  opiate receptor 5' region

<400> SEQUENCE: 3
gtaaggaaag cgccagggct ccgagcggag ggttcagcgg cttaaggggg tacaaagaga      60
cacctaactc ccaaggctca atgttgggcg ggaggatgaa agaggggagg taaactgggg    120
ggactctgga ggagaccacg gacagtgatt gttatttcta tgagaaaacc tacttttctg    180
ttttttcttc aactgataaa gaaagaattc aaaatttcag gagcagagaa gttgctttgg    240
taaaagctac aaatgtctag gggtgggggg cggagggaag ctatagcata gacttggagc    300
gcttccttat actgagcaaa gagggctctt ggcagagtcc tacactcagt ccctctgcag    360
gagctatgga aagagtaagt tgt                                             383

<210> SEQ ID NO 4
<211> LENGTH: 538
<212> TYPE: DNA
<213> ORGANISM: Artificial Sequence
<220> FEATURE:
```

```
<223> OTHER INFORMATION: Description of Artificial Sequence: Human
      Genomic Clone
<221> NAME/KEY: intron
<222> LOCATION: (1)..(538)
<223> OTHER INFORMATION: intron 1 of human  opiate receptor 3' region

<400> SEQUENCE: 4
aaaaaaaaaa ttaaaaccct cactgcgtgt ggtgtctcat gcctgtaaca caaacacttt     60
gggaggccga ggagggagga ctgcttgagc ccaagagttc aagaccaccc taagcaacat    120
gtcaagaccc tgtccctaca aaagtttttt aaaattaaca gggtatggtg gcatgcacct    180
gggatcccag ttattcagga ggtgaggcaa gaggatctct tgagtccagg aggttaaagc    240
tgtagtgagc tctgttcata ccattacact ccagcctggg taacagggca agatcctatc    300
caaaaaaaaa aaggaagaaa ctcaacaaag cagcatcgtt gctattattg cagctattta    360
gccaataggt acatcattga catcattgta aatagccaag ctgatactgg aaaacaattc    420
tatatctaat ctcaaaaaag ctttctacta atttcatgca aatttattat tggaagctta    480
cctatatttt acactagtgt cttttactga ttctcactct tcttccttta tctcctag      538

<210> SEQ ID NO 5
<211> LENGTH: 300
<212> TYPE: DNA
<213> ORGANISM: Artificial Sequence
<220> FEATURE:
<223> OTHER INFORMATION: Description of Artificial Sequence: Human
      Genomic Clone
<221> NAME/KEY: intron
<222> LOCATION: (1)..(300)
<223> OTHER INFORMATION: intron 3 of human  opiate receptor 5' region

<400> SEQUENCE: 5
gtacgcagtc tctagaatta ggtatatcta ctggggatga cataaaaatt ataaggcttt     60
gtgctaaact aggagtttaa tccattatag aggatgagaa tggagggaag aggggaagca    120
aattgtggtt ctagtgttag agaagaggtt tgttatataa actgtgttct ttatatttga    180
ctgtacatat tcatttaggt ataaagatac accaatgaga aatccatgaa actattcaaa    240
ataactattt ttatggcctt tacttctatg caaaaatttt atgactttag cacattatag    300

<210> SEQ ID NO 6
<211> LENGTH: 400
<212> TYPE: DNA
<213> ORGANISM: Artificial Sequence
<220> FEATURE:
<223> OTHER INFORMATION: Description of Artificial Sequence: Human
      Genomic Clone
<221> NAME/KEY: intron
<222> LOCATION: (1)..(400)
<223> OTHER INFORMATION: intron 3 of human  opiate receptor 3' region

<400> SEQUENCE: 6
tggtactgaa aaaacatcg  tttttctttc aaaatttga  tcaagtcata aatgatttga     60
ggctaaagag ggaggaagag ggtaaaaaaa ggggagaaa  gagtttcaat taaaatgtat    120 ttttttcaagg aaattatcaa taatctctct ataatgacta gtatacagtt cttttcagta    180
gcatacacaa atgaagagca tattcataat gagccagaag attattcata atgtctgaag    240
agattgatta atgtcttgac atttaagaaa aactgaggct tgcaggtgaa agtatacatg    300
aaggtcttca atgcagttct tacgagcaga gatgctcaac aaatgtgtgt tgcaaccgta    360
tctgaaatgt tcactgtctt tgctctttct ctcctttcag                          400
```

<210> SEQ ID NO 7
<211> LENGTH: 2162
<212> TYPE: DNA
<213> ORGANISM: Artificial Sequence
<220> FEATURE:
<223> OTHER INFORMATION: Description of Artificial Sequence: Human Genomic Clone
<223> OTHER INFORMATION: cDNA encoding human opiate receptor
<221> NAME/KEY: unsure
<222> LOCATION: (2063)
<223> OTHER INFORMATION: n = unknown
<221> NAME/KEY: unsure
<222> LOCATION: (2091)
<223> OTHER INFORMATION: n = unknown

<400> SEQUENCE: 7

| | | | | | |
|---|---|---|---|---|---|
| tgggagggggg | ctatacgcag | aggagaatgt | cagatgctca | gctcggtccc | ctccgcctga | 60 |
| cgctcctctc | tgtctcagcc | aggactggtt | tctgtaagaa | acagcaggag | ctgtggcagc | 120 |
| ggcgaaagga | agcggctgag | gcgcttggaa | cccgaaaagt | ctcggtgctc | ctggctacct | 180 |
| cgcacagcgg | tgcccgcccg | gccgtcagta | ccatggacag | cagcgctgcc | cccacgaacg | 240 |
| ccagcaattg | cactgatgcc | ttggcgtact | caagttgctc | cccagcaccc | agccccggtt | 300 |
| cctgggtcaa | cttgtcccac | ttagatggca | acctgtccga | cccatgcggt | ccgaaccgca | 360 |
| ccaacctggg | cggagagac | agcctgtgcc | ctccgaccgg | cagtccctcc | atgatcacgg | 420 |
| ccatcacgat | catggccctc | tactccatcg | tgtgcgtggt | ggggctcttc | ggaaacttcc | 480 |
| tggtcatgta | tgtgattgtc | agatacacca | agatgaagac | tgccaccaac | atctacattt | 540 |
| tcaaccttgc | tctggcagat | gccttagcca | ccagtaccct | gcccttccag | agtgtgaatt | 600 |
| acctaatggg | aacatggcca | tttggaacca | tcctttgcaa | gatagtgatc | tccatagatt | 660 |
| actataacat | gttcaccagc | atattcaccc | tctgcaccat | gagtgttgat | cgatacattg | 720 |
| cagtctgcca | ccctgtcaag | gccttagatt | tccgtactcc | ccgaaatgcc | aaaattatca | 780 |
| atgtctgcaa | ctggatcctc | tcttcagcca | ttggtcttcc | tgtaatgttc | atggctacaa | 840 |
| caaaatacag | gcaaggttcc | atagattgta | cactaacatt | ctctcatcca | acctggtact | 900 |
| gggaaaaccct | cgtgaagatc | tgtgttttca | tcttcgcctt | cattatgcca | gtgctcatca | 960 |
| ttaccgtgtg | ctatggactg | atgatcttgc | gcctcaagag | tgtccgcatg | ctctctggct | 1020 |
| ccaaagaaaa | ggacaggaat | cttcgaagga | tcaccaggat | ggtgctggtg | gtggtggctg | 1080 |
| tgttcatcgt | ctgctggact | cccattcaca | tttacgtcat | cattaaagcc | ttggttacaa | 1140 |
| tcccagaaac | tacgttccag | actgtttctt | ggcacttctg | cattgctcta | ggttacacaa | 1200 |
| acagctgcct | caacccagtc | ctttatgcat | ttctggatga | aaacttcaaa | cgatgcttca | 1260 |
| gagagttctg | tatcccaacc | tcttccaaca | ttgagcaaca | aaactccact | cgaattcgtc | 1320 |
| agaacactag | agaccacccc | tccacggcca | atacagtgga | tagaactaat | catcagctag | 1380 |
| aaaatctgga | agcagaaact | gctccgttgc | cctaacaggt | tctcatgcca | ttccgacctt | 1440 |
| caccaagctt | agaagccacc | atgtatgtgg | aagcaggttg | cttcaagaat | gtgtaggagg | 1500 |
| ctctaattct | ctaggaaagt | gcctactttt | aggtcatcca | acctctttcc | tctctggcca | 1560 |
| ctctgctctg | cacattagag | ggacagccaa | aagtaagtgg | agcatttgga | aggaaaggaa | 1620 |
| tataccacac | cgaggagtcc | agtttgtgca | agacacccag | tggaaccaaa | acccatcgtg | 1680 |
| gtatgtgaat | tgaagtcatc | ataaaaggtg | accttctgt | ctgtaagatt | ttattttcaa | 1740 |
| gcaaatattt | atgacctcaa | caagaagaa | ccatctttg | ttaagttcac | cgtagtaaca | 1800 |
| cataaagtaa | atgctaccctc | tgatcaaagc | accttgaatg | gaaggtccga | gtcttttag | 1860 |

-continued

```
tgtttttgca agggaatgaa tccattattc tattttagac ttttaacttc aacttaaaat    1920
tagcatctgg ctaaggcatc attttcacct ccatttcttg gttttgtatt gtttaaaaaa    1980
aataacatct ctttcatcta gctccataat tgcaagggaa gagattagca tgaaaggtaa    2040
tctgaaacac agtcatgtgt canctgtaga aaggttgatt ctcatgcact ncaaatactt    2100
ccaaagagtc atcatggggg attttcatt cttaggcttt cagtggtttg ttcctggaat     2160
tc                                                                   2162
```

GENOMIC SEQUENCE OF THE HUMAN μ-OPIOID RECEPTOR GENE AND THE VARIANTS, POLYMORPHISMS AND MUTATIONS THEREOF

BACKGROUND OF THE INVENTION

The present invention relates to the genomic sequence of the human μ-opioid receptor gene and its variants, polymorphisms and mutations and their use.

As is known, the human μ-opioid receptor controls pain perception, 'reward' mechanisms and further important physiological functions. It is the highly specific target for morphine, the classical painkiller in contemporary medicine. In addition, it is target for further medically important analgesics, anesthetics and therapeutics such as e.g. methadone and fentanyl and commonly used addictive substances such as e.g. heroin and methadone. A number of (patho) physiological, biochemical, pharmacological findings, and observations from μ-opioid receptor knock out mice demonstrate that the μ opioid receptor gene is playing a major role in analgesia and anesthesia, and in the development and maintenance of addictions (dependence on opiates, alcoholism and other forms of dependence). Therefore, variants in the regulating, coding and intronic regions of this gene may contribute to genetic risk for addictions. In addition, such variants may affect the responsiveness of this receptor to endogenous and exogenous receptor ligands.

Addictions are common diseases of international dimension and cause, in general, scarcely comprehensible grave economic damages to the amount of billions up to trillions, not to speak of the deleterious psychosocial consequences for the individual, his family and society.

The genomic sequence of the human μ opioid receptor gene is not known. So far only the cDNA of the μ opioid receptor gene has been described; the first cDNA of a μ opioid receptor was cloned by means of probes targeted against conserved regions of the δ opioid receptor from a rat cDNA gene bank by Chen et al. (Molecular cloning and functional expression of a mu opioid receptor from rat brain. Mol. Pharmacol. 44, 8–12, 1993), the first human MOR cDNA by Wang et al. (Mu opiate receptor: cDNA cloning and expression. Proc. Natl. Acad. Sci. U.S.A. 90, 10230–10234, 1993). The only promoter sequence so far known was cloned from a mouse gene bank (Min. et al., Genomic structure and analysis of promoter sequence of a mouse μ opioid receptor gene. Proc. Natl. Acad. Sci. U.S.A. 91, 9081–9085,1994).

Actual findings obtained from 'knockout' mice with an interrupted μ opioid receptor gene show clearly that the analgesic and 'reward' inducing and dependence inducing effects of morphine are brought about specifically through the μ-opioid receptor subtype, yet not through δ- and κ opioid receptor subtypes. Accordingly, the μ opioid receptor is mandatory for morphine action in vivo (Matthes et al., Loss of morphine-induced analgesia, reward effect and withdrawal symptoms in mice lacking the μ opioid receptor gene. Nature 383, 819–823, 1996). A series of pharmacological and other studies have shown that the μopioid receptor expressed in brain is of key importance for the development of tolerance, addiction and analgesia (Reisine, Neurotransmitter Receptors V., Neuropharmacology 34, 463–472, 1995). In this context, endorphins come into consideration as endogenous ligands. Exogenous μ opioid receptor ligands such as morphine, codeine, methadone and fentanyl have been used for a long time as analgesics and therapeutics in clinics.

As is known, the clinical use of opiates causes undesired side effects such as breathing disturbances, miosis, nausea and vomiting, sedation, depression and dependence.

It is the objective of the invention to identify and provide the genomic sequence of the human μ opioid receptor which may be used as basis for the development of specific and efficient analgesics, anesthetics and therapeutics for addiction, in particular for developing e.g. analgesics not having addictive side effects, or for developing diagnostic kits.

According to the invention it was possible to identify and provide the genomic sequence of the human μ opioid receptor gene and of variants, polymorphisms and mutants in specific populations.

DESCRIPTION OF THE PREFERRED EMBODIMENTS

The genomic DNA sequence of the human μ opioid receptor amplified and sequenced according to the invention consists of 1) a promoter region (incl. 5' regulatory region) SEQ ID no. 1 of a length of altogether 2412 bp.

The promoter is cloned according to methods known per se by amplifying the five various genomic DNA regions covering the human μ opioid receptor promoter region.

2) Intron 2 the genomic DNA sequence of which is between nucleotides 855 and 856 of the cDNA sequence (or between nucleotides 643 and 644 related to A of the translation starting point) of a length of 773 bp according to SEQ ID no. 2.

3) the 5' region of intron 1 the genomic DNA sequence of which is behind nucleotide 502 of the cDNA sequence (or behind nucleotide 290 related to the translation starting point) of a length of 383 bp according to SEQ ID no. 3; and the 3' region the genomic DNA sequence of which is in front of nucleotide 503 of the cDNA sequence (or in front of nucleotide 291 related to the translation starting point) of a length of 538 bp according to SEQ ID no. 4.

4) the 5' region of intron 3 the genomic DNA sequence of which is behind nucleotide 1376 of the cDNA sequence (or behind nucleotide 1164 related to the translation starting point) of a length of 300 bp according to SEQ ID no. 5; and the 3' region the genomic DNA sequence of which is in front of nucleotide 1377 of the cDNA sequence (or in front of nucleotide 1165 related to the translation starting point) of a length of 400 bP according to SEQ ID no. 6.

Sequencing of the intron is carried out analogously to sequencing of promoters.

In addition, there was detected that the human cDNA sequence already known consisting of 2162 bp is defective in the first 16 nucleotides. According to the invention the cDNA has SEQ ID no. 7.

The genomic sequence of the human μ opioid receptor gene is represented in illustrations 1a and 1b in a survey.

Four different transcription starting positions were identified in positions 212, 329, 371 and 421 bp upstream of the translation star site (ATG).

Variants, polymorphisms and mutants in specific populations are marked by base exchange. According to the invention these are base exchanges in up to 100 nucleotide positions, preferably up to 37 base exchanges are identified. In the cDNA region, in particular, preferably up to 20 base exchanges are identified, most preferably up to 11 base exchanges.

In a scheme according to the invention base exchanges take place in the following positions of the promoter (=RG= 5' regulatory region), of the exons (=cDNA sequence) and of the introns:

| Name | Exchange of nucleotides | Exchange of amino acids/ Splice variant | Region position | cDNA |
|---|---|---|---|---|
| −1793/4T→A | T→A at −1793/4 | | RG | |
| −1768ins22 | Insertion of 22 bp behind −1768 | | RG | |
| −1699insT | Insertion of T behind −1699 | | RG | |
| −1595T→C | T→C at −1595 | | RG | |
| −1565T→C | T→C at −1565 | | RG | |
| −1469T→C | T→C at −1469 | | RG | |
| −1320A→G | A→G at −1320 | | RG | |
| −1255A→T | A→T at −1255 | | RG | |
| −1236A→G | A→G at −1236 | | RG | |
| −1171A→G | A→G at −1171 | | RG | |
| −1045A→G | A→G at −1045 | | RG | |
| −995C→A | C→A at −995 | | RG | |
| −692G→C | G→C at −692 | | RG | |
| −665del3 | Deletion of 3 bp from −665 to −663 | | RG | |
| −554G→A | G→A at −554 | | RG | |
| −488G→T | G→T at −488 | | RG | |
| −254A→C | A→C at −254 | | RG | |
| −236A→G | A→G at −236 | | RG | |
| −172G→T | G→T at −172 | | Exon 1 | 41 |
| −133C→T | C→T at −133 | | Exon 1 | 80 |
| −111C→T | C→T at −111 | | Exon 1 | 102 |
| −38C→A | C→A at −38 | | Exon 1 | 175 |
| A6V(C→T) | C→T at 17 | Ala→Val at 6 | Exon 1 | 229 |
| N40D(A→G) | A→G at 118 | Asn→Asp at 40 | Exon 1 | 330 |
| N152D(A→G) | A→G at 454 | Asn→Asp bei 152 | Exon 2 | 666 |
| IVS2 + 31G→A | G→A at 643 + 31 | Putative splice variant | Intron 2 | |
| IVS2 + 106T→C | T→C at 643 + 106 | | Intron 2 | |
| IVS2 + 397T→A | T→A at 643 + 397 | | Intron 2 | |
| IVS2 + 438G→A | G→A at 643 + 438 | | Intron 2 | |
| IVS2 + 480T→C | T→C at 643 + 480 | | Intron 2 | |
| IVS2 + 534C→T | C→T at 643 + 534 | | Intron 2 | |
| IVS2 + 691G→C | G→C at 643 + 691 | | Intron 2 | |
| R265H(G→A) | G→A at 794 | Arg→His at 265 | Exon 3 | 1006 |
| S268P(T→C) | T→C at 802 | Ser→Pro at 268 | Exon 3 | 1014 |
| T314T(G→A) | G→A at 942 | Thr = Thr at 314 | Exon3 | 1154 |
| IVS3 + 37A→C | A→C at 1164 + 37 | | Intron 3 | |
| 1401G→C | G→C at 1401 | | Exon 4 | 1613 |

This exchange may be optionally effected only in one of the above-mentioned nucleotide positions, in any of the positions mentioned, or in all of the positions mentioned.

According to the invention such interindividual allelic variations in the coding and regulatory DNA regions of the human μ opioid receptor gene may be associated with individually different responsiveness to anesthetics/therapeutics and/or addictive substances, as well as an increased genetic risk for substance, dependence or e.g. physiologically modified pain sensitivity. Thus, they are used as a starting point for the development of individually tailored therapeutics, the prediction of individual therapeutic 'response' and the genetic risk of addiction, contributing thus, at the same time, to prevention. In addition, they are the starting point for the genotypification of individuals to examine relevant environmental factors for the development of addition on the long term.

Thus, according to the invention the sequences serve the development of therapeutics, in particular analgesics/anesthetics and drug-therapeutics. They are used for building up genes and vectors which form the basis for the development of these pharmaceutically relevant substances.

Apart from that, diagnostic test kits are provided for predicting the risk of addiction such as e.g. dependence on opiates, alcoholism, dependence on cocaine etc. or for predicting the individual responsiveness to various analgesics and/or anesthetics and for the individually differing disposition to side effects of pharmaceutics.

In further perfecting the invention is was detected that associations of variants detected in the μ opioid receptor gene occur with diseases or clinically relevant phenotypes.

A significant association/specific connection of the Asn→Asp mutation in position 40 of the amino acid sequence (position 330 of the cDNA sequence) with family-related alcoholism was detected. This sequence position is not only connected with alcoholism as a specific form of addiction but also with a general disposition to addiction as it finds its expression in man by the nearly usual, very frequently occurring clinical form of multiple drug dependence (here caused by the simultaneous abuse of alcohol, opiates and cocaine). In addition, this mutation results in a functional state of the human μ opiate receptor which leads to a modified responsiveness of the receptor to ligands (endogenous and exogenous ligands including therapeutics, anesthetics and drugs) and a modified responsiveness of the receptor to a prolonged or repeated application of these ligands, thus being of importance to the development of tolerance (desensitization of the receptor to a chronic administration of pharmaceuticals) and dependence.

Furthermore, there was detected that the specific combinations of variants in the 5' regulatory region are connected with a disposition to various diseases, in particular addictions. In particular, the positions −1793/4T→A, −1768ins22, −1699insT, −1469T→C, and −1320A→G are of relevance in this respect. Especially the combination −1793/4A, −1768 wild type, −1699insT, −1469T and −1320G is connected with a disposition to cocaine abuse and with a disposition to addiction in general (including alcoholism and dependence on opiates) and is functionally accompanied by a modified expression of the receptor. This combination described ('haplotype') can better describe the real, overall functional state of the receptor in the pathophysiological situation than an individual, associated variant. This analysis is based on the concept that the differing functional (dysfunctional) receptor states are not exclusively based on individual mutations but that they are also caused by the individual "polymorphic" total gene sequence (gene profile) as a unity determining the functions.

Accordingly, the object of the invention is a method for identifying the dispositions to diseases wherein the DNA of a proband is isolated and genotypied in selected positions and subsequently compared with the reference DNA sequence. Forms of execution where the positions −1793/4T→A, −1768ins22, −1699insT, −1469T→C and −1320A→G are genotypied are preferred.

To detect the disposition to addiction it will be sufficient if 3 of these 5 positions will be investigated, yet it would be preferable to genotype all 5 positions to obtain reliable data. Additionally, it is possible to investigate position 330 of the cDNA sequence in connection with a disposition to alcohol by means of the test method.

Genotypification is effected by sequencing or other methods suited for detecting point mutations. They involve PCR-based genotyping methods such as e.g. allele-specific-PCR, other genotyping methods using oligonucleotides and methods using restriction enzymes.

The method according to the invention allows a. o. to detect a disposition to family-related alcoholism, addiction to cocaine and a dependence on opiates. Furthermore, an individually differing responsiveness to receptor agonists and antagonists may be detected.

```
Promoter 2412 bp SEQ ID no. 1

TGTGTTAGTGAGCAGACCTCCCTTAGGAACCTTATTACGGAGTACAAAGCTAGGAGAGTAAATAA

AGTATATTAAAAAATGCATACAAAAGATGACAGAATCACCATTCCAAAAGATCTTGGTGGATAAG

AATCATGAATTGGATCTAACAAGATGTAACTTAAAAGTGAAAAAATCTATAGTGTTGTACTGAGC

TCCCTCCAAAGCAACTATAAATTTATAGGAGATGAAACATATGATTCACCAGGCATAAGAAGAAA

GTTTCCGTAATCAAACACTATTGTATCCATCTTTTTAAACTCCAGCTCCTATCACAGCACCTGGT

CCAAAGCAGATCTTTAGTATTTGTGGAACTGGCTTGGATTGTGTTTAGGAAATTTTGTCATTGGT

AAACCTAAGGAGAGTCAAGAGAACAACGTGACCAAAAAATAAAACTAAAAAAAAAAAAAAGGGAC

TTTCATTGTACTGGTAGAAAGACAAAGTTTATAATCTGGCTTAGTTTCTTTTTTTGTTGTTGTTT

GTTTTTTGGTCAGGGCAAATTTAGGTCATTATTTTTAACACTGGAACTGTAGTTTCAGAGCAGAT

AGACAAACTATCAATGAGAATAGATGAACAGCAAGGCCACTGAAAGGACTCAGAACTACATCTTA

TAAGAAACAACTGAATGATGCTAATGTTTAACTTGCAAAAGAGAAAACTCAGTTGATTTCAAATA

TATGAAATATAGTGGTAAGGAGTTATCACTTATTAAGCAATTACTATTGCAATGTATACTCATTT

AATCCTGCTAACAGACATATGAGGTGAATATTATTAGCCTACCCTCGCCTTTTTAAGTAATGAG

AAGACTGTCATCCTGTAGGGTAAAGTAACATGTCCAAACTCATACAGCTACAAAGTTACAAAGCT

GATTTATAAAATGATTGACTCCAAGGTCAGGAATTATTATACTGTGTCTTGTCTTCCACATGAAC

TAAGCACAAAGGAACTGAATGCAGGCAGACAGATTTCAGCTCAATATAAGAGAATTGTTACATTA

GTTCATGGAAGAATATGTTTTAAGGTATTTTTGTTAGTCTCTAGGAAATCTCTGTAACATTTTAT

TGTGTAAATTATATGCTTTAATGTAAGAGGATAAAAATAATAGTGAACATTGGCAAAATAGCCTA

TGATTAATAGAGTTTACCTATGAGTTATCTGTTTCTAAGATAAATGCCAAAAAATAATATTGGAA

TTAAATGTTCCTTTCAAGATCTTCCCTCCCTGCTCCCTGAAATTGCAGTGAATTTTTCAAGACCA

ACTGAGGACATGTATTTTCAATGTTTATGGTTAAAAGATATGTACATGCACAGATATATACATGT

ACAGAAATGAGAATTACTTCAGAATTGGTGTTAACTTTAGAAAAAAAAAGACCAAGAACTTACTC

TTGGTATTTACAAATTTATTTCTAAAATAGAAGCACTCATGGACTTAGAAGTAAGGTATAAAATT

CAAAAACGTATCCATGTTTCTCAAGGATCTTGTTGTAGGCCACTCTAATTCCATATATTATGTGG

CTTTTCCTAGAATTTTTACACTAGAAAACAGACTGAATGCAAATTTTGTTTTGTTTTAACAACCT

TCTTCTCAGAAGCATATGTCTATCGAGGAAGTCTTCAGATAAAAAAGATAAACAATTCCAAACAG

GTCTATGAGATTTAAGATGTGAAAGATCAACATTATCTTTAGTTGACTTTACTGGATGCCACAAC

CTTCTGATTTCTGTAACCACTTCTTATGCCTCCTACCCACTGAAACAAAATCAGAGGCAAACAGA

GCTTCACCCTAGAAATTGGGGAAAATGAGGAACAGGTTTTCTGCACAAAAGTTTATTTGTTTCTC

ATTTCTTTTTCAGAAAATAAAGGATCGCTGTTGTTCCCAACAGGTTTGTAGGGAAGAAAATTGGA

GAAACATTATTACCTTTTCTTAGATGTTGGCAACGGAGGCAACAAGGACTGCAAAAGAAAATTGT

GTGTCCCCATTCCTAAATAATCAAAATTGGCAGTAGGGATGGAAGAGCATTGGGGTTTTAGGGC

TGTTAGGGTTTCATCAAGCCAATGTATTCCCTGCCAGATTTTAAGGAGAAAAAGGCGCTGGAAAA

TTGAGTGATGTTAGCCCCCTTTCTTATTTTTGCACTGCTACCAAAGACTAACTCTATCTCTCTCC

CCAACCCTTCTCTCCATCTCCCTCCTTTAGATGTGTTTGCACAGAAGAGTGCCCAGTGAAGAGAC

CTACTCCTTGGATCGCTTTGCGCAAAATCCACCCCTTTTCCCTCCTCCCTCCCTTCCAGCCTCCG
```

-continued

AATCCCGCATGGCCCACGCTCCCCTCCTGCAGCGGTGCGGGGCAGGTGATGAGCCTCTGTGAACT
ACTAAGG                                                     2412

SEQ ID no. 2 - Intron 2

GTGAGTGATGTTACCAGCCTGAGGGAAGGAGGGTTCACAGCCTGATATGTTGGTGATGTCATAAG
CAAAGCAGTATTTATGGAGTGCCCCATTGTCTTAGTCACATTGTAATTTTAATTATTCTTCCTAG
CAAAAAAAGCCTTTGAATACTTAAAAATAGGAATTTTCCTCATAATTTTAGGCCTATTAAATCCT
TTAAAGAGAATGTAATCTATTTATTTCTGATTTCTCTGTATTTACTTCATAAAAATGGTGTGTAA
ATTAGTACATAGCTCTCCCAAGAGTAATTGGAGCTTAAACCCAAAGAGTATTACACTGAGGCTTG
TTTAAAATTATCAAGTGGCTGACTACATGGCAAATGTATCTTTCTACACCTAATATCAGAATATT
GAACAATCCATCAAAAAATGAAGTGAAAACATCCATTACCTGGAGCCGCCTAGAGACTTTGGACA
ATTATTACATTTTTTATATCAATATAGACCTCATGGAGGATCTAGCTCATGTTGAGAGGTTCATT
TTTGTTCCCTGAACGAAAGCTTAATGTGATCGAAGTGGACTGCAAAATGGGAAATTTAGAAAAAA
ACAAAAAACATTAGAAGTAAAACTTTCTTTGAAAAGTAACAAACAACTGAGTTTCTTCCACAATT
TCTTTATAGCCTTAAGTTAGCTCTGGTCAAGGCTAAAAATGAATGAGCAAAATGGCAGTATTAAC
ACCTTATGACATAATTAAATGTTGCTGCTAATTTTTCCTTTAAATTCCTTTCTTCTAG
                                773

SEQ ID no. 3 - Intron 1 5' region

GTAAGGAAAGCGCCAGGGCTCCGAGCGGAGGGTTCAGCGGCTTAAGGGGGTACAAAGAGACACCT
AACTCCCAAGGCTCAATGTTGGGCGGGAGGATGAAAGAGGGGAGGTAAACTGGGGGACTCTGGA
GGAGACCACGGACAGTGATTGTTATTTCTATGAGAAAACCTACTTTTCTGTTTTTTCTTCAACTG
ATAAAGAAAGAATTCAAAATTTCAGGAGCAGAGAAGTTGCTTTGGTAAAAGCTACAAATGTCTAG
GGGTGGGGGCGGAGGGAAGCTATAGCATAGACTTGGAGCGCTTCCTTATACTGAGCAAAGAGGG
CTCTTGGCAGAGTCCTACACTCAGTCCCTCTGCAGGAGCTATGGAAAGAGTAAGTTGT
                                383

SEQ ID no. 4 - Intron 1 3' region

AAAAAAAAAATTAAAACCCTCACTGCGTGTGGTGTCTCATGCCTGTAACACAAACACTTTGGGAG
GCCGAGGAGGGAGGACTGCTTGAGCCCAAGAGTTCAAGACCACCCTAAGCAACATGTCAAGACCC
TGTCCCTACAAAAGTTTTTTAAAATTAACAGGGTATGGTGGCATGCACCTGGGATCCCAGTTATT
CAGGAGGTGAGGCAAGAGGATCTCTTGAGTCCAGGAGGTTAAAGCTGTAGTGAGCTCTGTTCATA
CCATTACACTCCAGCCTGGGTAACAGGGCAAGATCCTATCCAAAAAAAAAAAGGAAGAAACTCAA
CAAAGCAGCATCGTTGCTATTATTGCAGCTATTTAGCCAATAGGTACATCATTGACATCATTGTA
AATAGCCAAGCTGATACTGGAAAACAATTCTATATCTAATCTCAAAAAAGCTTTCTACTAATTTC
ATGCAAATTTATTATTGGAAGCTTACCTATATTTTACACTAGTGTCTTTTACTGATTCTCACTCT
TCTTCCTTTATCTCCTAG                         538

SEQ ID no. 5 - Intron 3 5' region

GTACGCAGTCTCTAGAATTAGGTATATCTACTGGGGATGACATAAAAATTATAAGGCTTTGTGCT

-continued

```
AAACTAGGAGTTTAATCCATTATAGAGGATGAGAATGGAGGGAAGAGGGGAAGCAAATTGTGGTT

CTAGTGTTAGAGAAGAGGTTTGTTATATAAACTGTGTTCTTTATATTTGACTGTACATATTCATT

TAGGTATAAAGATACACCAATGAGAAATCCATGAAACTATTCAAAATAACTATTTTTATGGCCTT

TACTTCTATGCAAAAATTTTATGACTTTAGCACATTATAG                          300
```

SEQ ID no. 6 - Intron 3 3' region

```
TGGTACTGAAAAAAACATCGTTTTTCTTTCAAAATTTTGATCAAGTCATAAATGATTTGAGGCTA

AAGAGGGAGGAAGAGGGTAAAAAAAGGGGGAGAAAGAGTTTCAATTAAAATGTATTTTTTCAAGG

AAATTATCAATAATCTCTCTATAATGACTAGTATACAGTTCTTTTCAGTAGCATACACAAATGAA

GAGCATATTCATAATGAGCCAGAAGATTATTCATAATGTCTGAAGAGATTGATTAATGTCTTGAC

ATTTAAGAAAAACTGAGGCTTGCAGGTGAAAGTATACATGAAGGTCTTCAATGCAGTTCTTACGA

GCAGAGATGCTCAACAAATGTGTGTTGCAACCGTATCTGAAATGTTCACTGTCTTTGCTCTTTCT

CTCCTTTCAG                                                       400
```

SEQ ID no. 7 - cDNA

```
tgggaggggggctatacgcagaggagaatgtcagatgctcagctcggtcccctccgcctgacgctc ctctctgtctcagccaggactggtttctgtaagaaacagcaggagctgtggcagcggcgaaagga agcggctgaggcgcttggaacccgaaaagtctcggtgctcctggctacctcgcacagcggtgccc gcccggccgtcagtaccatggacagcagcgctgcccccacgaacgccagcaattgcactgatgcc ttggcgtactcaagttgctccccagcacccagccccggttcctgggtcaacttgtcccacttaga tggcaacctgtccgacccatgcggtccgaaccgcaccaacctgggcgggagagacagcctgtgcc ctccgaccggcagtccctccatgatcacggccatcacgatcatgccctctactccatcgtgtgc gtggtggggctcttcggaaacttcctggtcatgtatgtgattgtcagatacaccaagatgaagac tgccaccaacatctacatttttcaaccttgctctggcagatgccttagccaccagtaccctgccct tccagagtgtgaattacctaatgggaacatggccatttggaaccatcctttgcaagatagtgatc tccatagattactataacatgttcaccagcatattcaccctctgcaccatgagtgttgatcgata cattgcagtctgccaccctgtcaaggccttagatttccgtactccccgaaatgccaaaattatca atgtctgcaactggatcctctcttcagccattggtcttcctgtaatgttcatggctacaacaaaa tacaggcaaggttccatagattgtacactaacattctctcatccaacctggtactgggaaaacct cgtgaagatctgtgttttcatcttcgccttcattatgccagtgctcatcattaccgtgtgctatg gactgatgatcttgcgcctcaagagtgtccgcatgctctctggctccaaagaaaaggacaggaat cttcgaaggatcaccaggatggtgctggtggtggtggctgtgttcatcgtctgctggactcccat tcacatttacgtcatcattaaagccttggttacaatcccagaaactacgttccagactgtttctt ggcacttctgcattgctctaggttacacaaacagctgcctcaacccagtcctttatgcatttctg gatgaaaacttcaaacgatgcttcagagagttctgtatcccaacctcttccaacattgagcaaca aaactccactcgaattcgtcagaacactagagaccacccctccacggccaatacagtggatagaa ctaatcatcagctagaaaatctggaagcagaaactgctccgttgccctaacagggtctcatgcca ttccgaccttcaccaagcttagaagccaccatgtatgtggaagcaggttgcttcaagaatgtgta ggaggctctaattctctaggaaagtgcctactttttaggtcatccaacctctttcctctctggcca ctctgctctgcacattagagggacagccaaaagtaagtggagcatttggaaggaaaggaatatac
```

-continued

```
cacaccgaggagtccagtttgtgcaagacacccagtggaaccaaaacccatcgtggtatgtgaat tgaagtcatcataaaaggtgacccttctgtctgtaagattttattttcaagcaaatatttatgac ctcaacaaagaagaaccatcttttgttaagttcaccgtagtaacacataaagtaaatgctacctc tgatcaaagcaccttgaatggaaggtccgagtcttttagtgttttgcaagggaatgaatccat tattctattttagactttaacttcaacttaaaattagcatctggctaaggcatcattttcacct ccatttcttggttttgtattgtttaaaaaaaataacatctctttcatctagctccataattgcaa gggaagagattagcatgaaaggtaatctgaaacacagtcatgtgtcanctgtagaaaggttgatt ctcatgcactncaaatacttccaaagagtcatcatgggggattttcattcttaggctttcagtg gtttgttcctggaattc                                     2162
```

EXAMPLE 1

Generation of the Promoter Sequence According to SEQ ID No. 1

The amplification of the five different genomic DNA regions covering the promoter region of the human μ opioid receptor is effected with the aid of the promoter finder DNA walking kit from Clontech.

The kit consists of five various gene banks cleaved by a specific restriction endonuclease at the ends of which adapters were ligated. The specific 'adapter primer' (AP1) with the sequence 5'-GTAATACGACTCACTATAGGGC-3' and the gene specific primer (GSP1) MOR1X-R229G with the sequence 5'-GCAATTGCTGGCGTTCGTGGGGG-3' or MOR1X-R330T with the sequence 5'-CGGTTCGGA-CCGCATGGGTCGGACAGGTT-3' were used for the first PCR.

The PCR conditions were as follows: 10×Tth PCR buffer (400 mM Tris-HCl, 150 mM KOAc, pH 9.3), 10 mM dNTPs, 25 mM Mg(OAc)₂, 10 μM AP1, 10 μM GSP1, advantage Tth polymerase (5 U) and always an EcoRV-, ScaI-, DraI-, PvuII- or SspI gene bank.

The first PCR was carried out in a Perkin Elmer thermocycler 9600 as follows:

7 cycles: 94° C. for 2 sec, 72° C. for 3 min; 32 cycles: 94° C. for 2 sec, 67° C. for 3 min, finally 67° C. for 4 min.

The first PCR was diluted with dist. H₂O at a ratio of 1:50.

The 'nested' 'adapter primer' (AP2) with the sequence 5'-ACTATAGGGCACGCGTGGT-3' and the 'nested' gene specific primer (GSP2) MOR1X-P1 with the sequence 5'-GACCGAGCTGAGCATCTGACATTC-3' or MOR1X-R229G with the sequence 5'-GCAATTGCTGGC-GTTCGTGGGGG-3' were used for the second PCR.

The PCR conditions were as follows: 10×Tth PCR buffer (400 mM Tris-HCl, 150 mM KOAc, pH 9.3), 10 mM dNTPs, 25 mM Mg(OAc)₂, 10 μM AP2, 10 μM GSP2, advantage Tth polymerase (5 U) and the five diluted gene banks.

The second PCR was carried out in a Perkin Elmer thermocycler 9600 as follows: 5 cycles: 94° C. for 2 sec, 72° C. for 3 min; 20 cycles: 94° C. for 2 sec, 67° C. for 3 min, finally 67° C. for 4 min.

The five various fragments were electrophoretically separated on a 2% agarose gel. The fragments had a size of approx. 2.8 kb using the AscI gene bank, approx. 2.6 kb using the DraII gene bank, approx. 1.6 kb using the SspI gene bank, approx. 1.5 kb using the PvuII gene bank and approx. 1.2 kb using the EcoRV gene bank. Sequencing was effected with the aid of the thermosequenase 'cycle sequencing kits' from Amersham. The second PCR primers were used as sequencing primers and successively new primers were synthesized. By means of the same strategy the genomic DNA sequences in the 5' and 3' regions of intron 1 were cloned according to SEQ ID no. 3 and SEQ ID no. 4 and of intron 3 according to SEQ ID no. 4 and of intron 3 according to SEQ ID no. 5 and SEQ ID no. 6.

EXAMPLE 2

By means of an analogous strategy the genomic DNA sequence of intron 2 was cloned according to SEQ ID no. 2.

What is claimed is:

1. An isolated and purified genomic DNA sequence comprising the nucleotide sequence of SEQ ID NO. 1, said sequence encoding a regulatory region of a human µ-opioid receptor gene.

2. The genomic sequence according to claim 1, wherein the base substitution is T→A, and occurs at position −1793/4 of SEQ ID NO. 1.

3. The genomic sequence according to claim 1, further comprising a promoter region according to base pairs 1−2412 of SEQ ID NO. 1.

4. The genomic sequence according to claim 1, wherein the sequence comprises one or more nucleotide sequence variations, wherein the one or more variations are selected from the group consisting of:

i. a 22 base pair insertion behind position −1768,
  ii. an insertion of T behind −1699,
  iii. T→C at −1595,
  iv. T→C at −1565,
  v. T→C at −1469,
  vi. A→G at −1320,
  vii. A→T at −1255,
  viii. A→G at −1236,
  ix. A→G at −1171,
  x. A→G at −1045,
  xi. C→A at −995,
  xii. G→C at −692,
  xiii. deletion of 3 base pairs from −665 to −663,
  xiv. G→A at −554,
  xv. G→T at −488,
  xvi. T→A at −1793/4
  xvii. A→C at −254, and
  xviii. A→G at −236.

* * * * *